United States Patent [19]

Giovinazzo

[11] Patent Number: 4,710,195

[45] Date of Patent: Dec. 1, 1987

[54] POSTERIOR CHAMBER INTRAOCULAR LENS

[76] Inventor: Vincent J. Giovinazzo, 299 Lighthouse Ave., Staten Island, N.Y. 10306

[21] Appl. No.: 853,551

[22] Filed: Apr. 18, 1986

[51] Int. Cl.$^4$ .............................................. A61F 2/16
[52] U.S. Cl. ................................................ 623/6
[58] Field of Search ........................................... 623/6

[56] References Cited

U.S. PATENT DOCUMENTS

| | | | |
|---|---|---|---|
| 4,254,510 | 3/1981 | Tennant | 623/6 |
| 4,363,143 | 12/1982 | Callahan | 623/6 |
| 4,424,597 | 1/1984 | Schlegel | 623/6 |
| 4,435,855 | 3/1984 | Pannu | 623/6 |
| 4,629,460 | 12/1986 | Dyer | 623/6 |

FOREIGN PATENT DOCUMENTS

WO85/02995 7/1985 PCT Int'l Appl. .................... 623/6
2151371A 7/1985 United Kingdom .................... 623/6

Primary Examiner—Ronald L. Frinks
Attorney, Agent, or Firm—McAulay, Fields, Fisher, Goldstein & Nissen

[57] ABSTRACT

A posterior chamber intraocular lens is usable as an implant in patients having both cataracts and glaucoma. The lens includes an optic portion which is capable of performing the focusing function of a human lens. Two haptics are connected to the optic. At least one of the haptic includes a blocking segment. The blocking segment has a length and width sufficient to prevent tissue posterior to a trabeculectomy fistula from occluding the fistula. The blocking segment thus creates a barrier to prevent the posterior chamber and other eye structures from interferring with proper drainage of aqueous humor from an eye.

5 Claims, 6 Drawing Figures

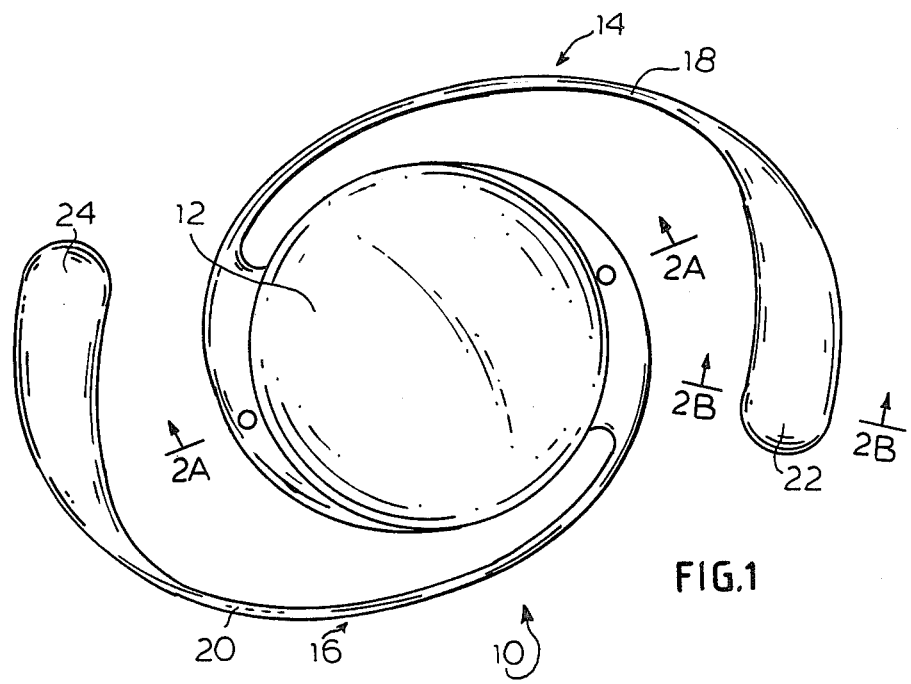
FIG.1
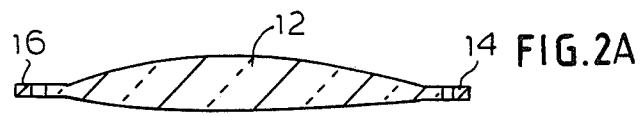
FIG.2A
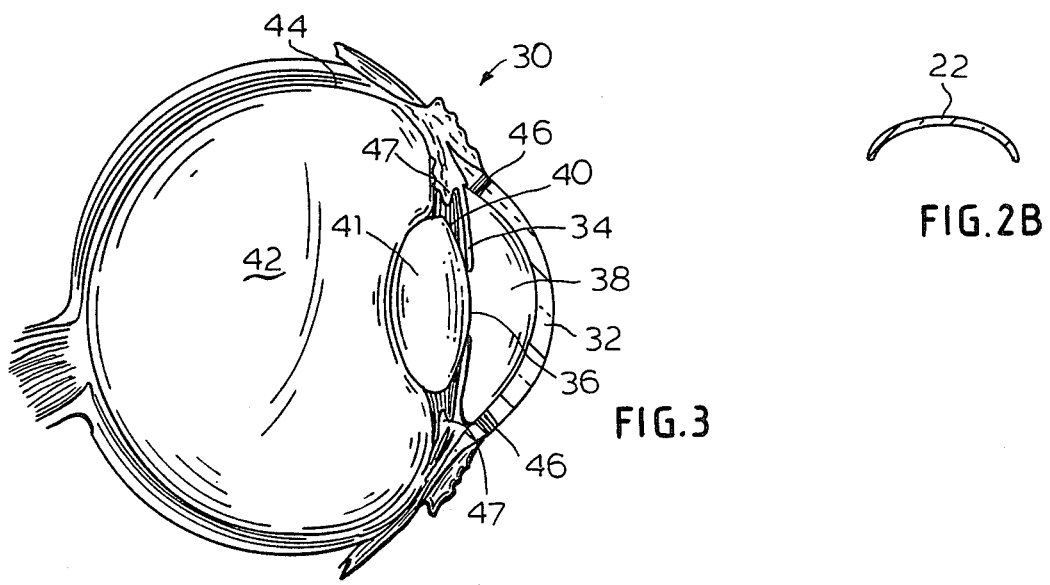
FIG.2B
FIG.3

POSTERIOR CHAMBER INTRAOCULAR LENS

BACKGROUND OF THE INVENTION

This invention relates to an intraocular lens for implantation in the posterior chamber of a human eye and more particularly to such a lens for use with patients having both glaucoma and cataracts.

Intraocular lens implantation in either the anterior chamber or the posterior chamber of the human eye is a known technique for treating cataracts. Opacification of the human lens (the development of cataracts) is a common problem which becomes more acute with age. By the age of 70, approximately ninety percent of the population suffers substantial loss of vision due to lens changes. Although cataracts are most often associated with age, they are also associated with certain medical conditions such as diabetes, hypocalcaemia and uraemia.

To restore vision to a patient with cataracts, the lens of the eye is surgically removed. Once removed, another mechanism must be substituted to perform the focusing function of the lens. In the past, a thick spectacle lens or a contact lens has been used after cataract surgery. More recently intraocular lens implants have been used.

There are generally two types of intraocular implant lenses, anterior chamber lenses and posterior chamber lenses. Both types of intraocular lens use an optic with associated haptics. The haptics help to place and stabilize the optic, which performs the functions previously performed by the human lens.

Two different techniques can be used for lens extraction, intracapsular extraction or extracapsular extraction. Intracapsular extraction removes the entire lens structure. In contrast, extracapsular extraction removes the anterior capsule and the cortex material of the lens while leaving in place the posterior lens capsule. The posterior lens capsule is essentially a membrane. Anterior chamber lenses must be used when intracapsular extraction is performed. When extracapsular extraction is performed, although either a posterior chamber or an anterior chamber lens may be used, the lens of choice is the posterior chamber lens.

Generally, extracapsular extraction is preferred. This is especially so when the patient also suffers from glaucoma since the anterior chamber lens causes various complications in patients with glaucoma which are not caused by posterior chamber lenses. Additionally, extracapsular extraction has the advantage of providing a capsular support for the intraocular lens and this type of extraction diminishes complications resulting from vitreous loss, such as retinal detachment and cystoid macular edema.

Under normal circumstances, the ciliary body of the eye produces aqueous humor which supplies nutrients to the lens and the cornea and which maintains normal intraocular pressure. The aqueous humor circulates from the posterior chamber through the pupil and into the anterior chamber. It then drains through the trabecular meshwork into the Canal of Schlemm, and from there through the aqueous veins into the venous system.

Glaucoma is a symptom characterized by an increase in intraocular pressure associated with abnormalities in either the formation or the outflow of aqueous humor. Left untreated this increased pressure leads to optic nerve damage with corresponding visual field loss. It is estimated that 2% of the general population and 5% of the population over the age of 65 have glaucoma. Although medical treatment may be used effectively in many cases of glaucoma, frequently a trabeculectomy must be performed to create a fistula in the trabecular meshwork which permits free passage of aqueous humor from the anterior chamber into the subconjunctival space to alleviate pressure. In order for the surgery to be effective, the fistula must remain substantially unobstructed.

The occurrence of glaucoma in a patient with cataracts is not an unusual one in ophthalmology. Both are diseases that are age related and occur with high frequency in the elderly population. In one large series of patients undergoing cataract extraction, glaucoma was found to be present in 4%. It has been found that the incidence of both glaucoma and cataracts increases with age. Between the ages of 52 and 64, there is a 1.4% incidence of chronic open angle glaucoma and a 4.6% incidence of cataract or aphakia. Between the ages of 65 and 74, the incidence of glaucoma rises to 5.1% and that of cataract rises to 18.1%. In the next decade (75 to 85 years), the incidence of glaucoma is 7.2% and the incidence of cataract or aphakia is 46.1%. There is a progressive increase in the incidence of both these diseases during the process of aging. Several other factors further increase the association of cataracts and glaucoma. Previous surgery for glaucoma, whether either a peripheral iridectomy or glaucoma filtration surgery, will hasten the development of a cataract. The use of strong miotics such as phospholine iodide is also implicated in the development of cataracts. The use of miotics in treating glaucoma also induces an earlier onset of symptoms, because of a small pupil, in patients with early cataractous changes of their lens. This can make cataract surgery necessary at an earlier stage in many glaucoma patients. With approximately 1,200,000 patients undergoing cataract implant lens surgery during 1985, approximately 50,000 of these patients will have concomitant glaucomatous eye diseases.

While glaucoma had been considered earlier a relative contraindication to intraocular lens implantation, many reports have suggested that the use of extracapsular extraction and posterior chamber lenses do not interfere with post-operative control of glaucoma. Rather, studies have indicated that posterior chamber intraocular lens implantation had no effect on the incidence of post-operative intraocular pressure elevations. The incision in extracapsular extraction is smaller and hence disturbs less conjunctiva which may be used later in filtration surgery. Less trabecular meshwork is distorted by suture closure which may help minimize early post-operative pressure elevations. Implant lenses are beneficial for patients with glaucoma and visual field defects as the minimum magnification resulting from such lenses allow more visual information to be presented than would occur with magnification of a scotoma resulting from aphakic spectacles or contact lens correction.

Patients who have glaucoma are always at risk for developing an intolerance to medical therapy or laser therapy and may eventually require a filtration operation for control of their intraocular pressure. All these operations involve creating a fistula between the subconjunctival space and the anterior chamber. This is made in various ways by creating a hole at the limbus by either cutting out a portion of the limbal tissues with either a scalpel blade or creating this fistula by burning with a cautery through the subconjunctival space into the anterior chamber. Fluid then filters through this fistula and is either gradually absorbed by vessels within the conjunctiva or gradually filters through the conjunctival tissues to be extruded externally with the tears. Planning and undertaking cataract surgery in an eye with glaucoma is extremely important because the management of glaucoma in the aphakic eye is difficult and frequently unsuccessful. One of the major antiglaucomatous medications, epinephrine, will cause in 20% of aphakic patients cystoid macular edema. While this maculopathy is usually reversible in the early stages, this must be considered a relative contraindication to the use of this drug in patients with glaucoma who are aphakic. The limitation of medical options only makes this problem more difficult because the surgical treatment of aphakic glaucoma has an extremely low success rate. Several studies on the success rate of standard filtration surgery range from 25 to 60%. One study with the success rate of 75% combined trabeculectomy surgery with a total vitrectomy. All these studies have evaluated patients whose aphakia was intracapsular in origin. Patients treated now and in the future will more likely have an extracapsular aphakia, and more probably an extracapsular aphakia with a posterior chamber lens. The cause of the poor results of filtration surgery in intracapsular aphakic glaucoma are not clear. Three possible reasons are proposed: 1. scarring of the conjunctival tissue resulting in inadequate bleb formation for filtration of fluid through the conjunctiva; 2. mechanical plugging of the filtering fistula by vitreous and/or ciliary processes; and 3. technical difficulties because of the complexity of the surgery.

The use of extracapsular surgery has brought hope that some of these problems can be alleviated. Separation of the vitreous from the aqueous by the posterior capsule may inhibit some induced change in the aqueous humor that makes it more fibrogenic in nature. This may reduce the incidence of scarring in the subconjunctival space and lead to better filtering of fluid and better bleb formation in the conjunctiva. The presence of a posterior capsule that is intact has been theoretically proposed as an effective barrier to the movement of vitreous which can cause an external plugging of the sclerostomy or the fistula site.

The posterior capsule after extracapsular surgery is diaphenous and extremely mobile. The posterior capsule and the vitreous which sits beneath it is readily moveable and will frequently create adhesions to the iris without the presence of an implant lens. In fact, patients with high myopia are recommeded by many to have an implant lens not for optical correction but to prevent the mobility of the posterior capsule. This mobility and subsequent anterior-posterior movement of the vitreous removes many of the benefits of extracapsular surgery. While the 6 to 7 mm. optic of a posterior chamber lens prevents this mobility centrally, it does nothing for this mobility in the far periphery of the posterior capsule. This is the area of concern in patients with glaucoma for this is where the fistula site is created during the performance of a glaucoma filtration operation. Here in the periphery, the mobility of the posterior capsule can readily plug a filtration site. In fact, if all the cortex is not removed during an extracapsular operation it too can plug and occlude a fistula site during concurrent or subsequent glaucoma filtration surgery. This plugging of the fistula site can be an important factor in the disappointing results in aphakic filtration surgery.

The biggest difference between filtration surgery in phakic and aphakic eyes is the lack of the normal lens-iris diaphragm in the periphery that exists in phakic eyes undergoing filtration surgery. The success rate of filtration surgery in phakic eyes is estimated from 75 to 95%.

It is evident that extracapsular extraction with a posterior chamber lens is desirable in patients with glaucoma who must undergo cataract surgery. Certainly, it has been shown that the results of filtration surgery in patients with aphakia of the intracapsular type is extremely disappointing. Scarring at the conjunctival site is a problem that is largely being solved with the use of antimetabolities such as 5-fluorouracil injected subconjunctivally. Plugging of the filtration sites is a problem that has not been solved by extracapsular surgery. Structures in the eye that can block this filtration site include the ciliary processes (this occurred also with intracapsular aphakia), retained cortical material, and the posterior capsule itself which remains mobile in the periphery.

Accordingly, it is a purpose of this invention to provide a posterior chamber intraocular lens which can be effectively used with glaucoma patients.

It is another purpose of this invention to provide such a lens which prevents the posterior capsule and ciliary process from occluding a fistula created in the trabecular meshwork.

Still another purpose of this invention is to provide such a lens, which is easily usable by surgeons and which does not create any additional complications for patients.

BRIEF DESCRIPTION

In brief, one embodiment of this invention involves a posterior chamber intraocular lens having an optic with two associated haptics. Each haptic includes a blocking segment. The blocking segment is shaped and dimensioned to act as a barrier capable of preventing the posterior capsule and ciliary process of the eye from moving and accidently occluding a trabeculectomy fistula. Thus, the blocking portion prevents inadvertent interference with drainage of the aqueous humor from the trabeculectomy incision.

BRIEF DESCRIPTION OF THE DRAWINGS

FIG. 1 is an enlarged top plan view of the intraocular lens of the present invention.

FIG. 2A is a sectional view taken generally along line 2A—2A of FIG. 1 and showing the optic portion of the FIG. 1 lens.

FIG. 2B is a sectional view taken generally along line 2B—2B of FIG. 1 and showing the blocking portion of one of the haptics of the FIG. 1 lens.

FIG. 3 is an enlarged cross-sectional view of a human eye.

DESCRIPTION OF THE PREFERRED EMBODIMENTS

As shown in the Figures, the posterior chamber implant lens 10 of the present invention includes an optic 12 with two associated flexible haptics 14, 16. The lens is a single piece construction made of polymethylmethacrylate (hereinafter PMMA). The optic 12 of lens 10 is conventional in the art and when the lens 10 is implanted in the eye, the optic 12 performs the focusing function of the human lens. Lens 10 is utilized as an implant lens when an extracapsular extraction has been performed.

Figure 4:
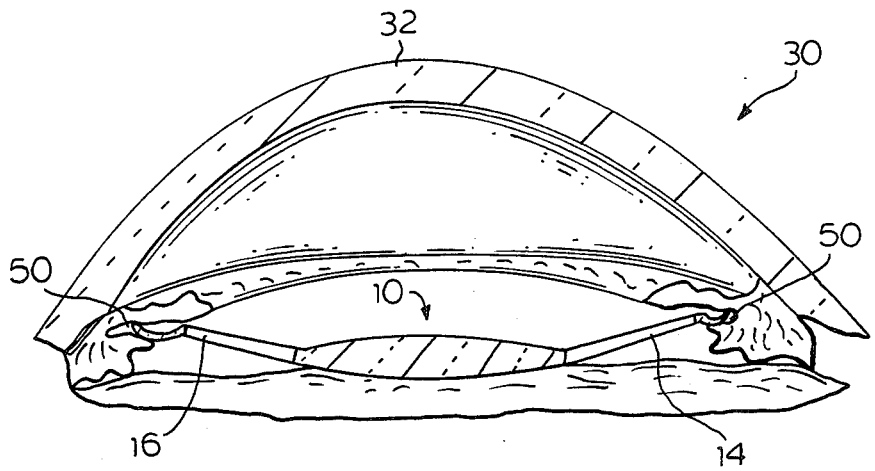
FIG. 4 is a schematic view showing an embodiment of the intraocular lens of the present invention in place in a human eye with the haptic portions resting in the ciliary sulcus.
Figure 5:
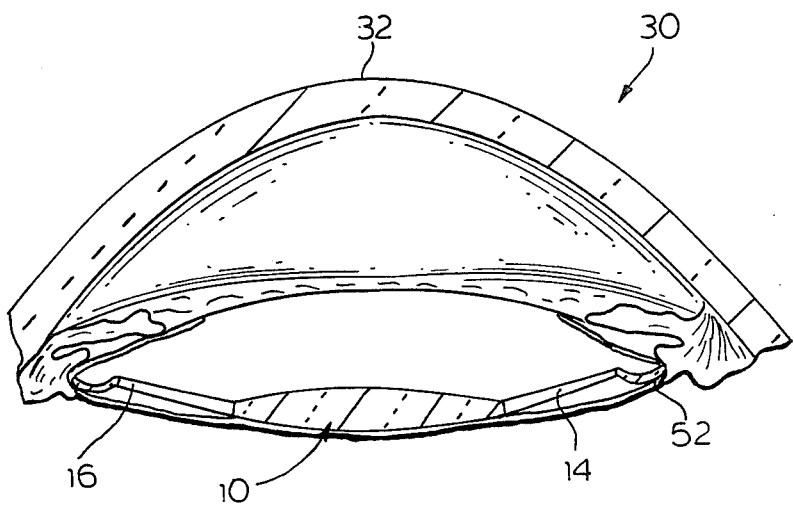
FIG. 5 is a view substantially similar to FIG. 4 but showing the haptics resting in the capsular bag.

As shown in FIGS. 4 and 5, lens 10 is implanted in a human eye 30 and the haptics 14,16 are vaulted in an anterior direction away from the optic. The eye includes a cornea 32 and an iris 34 having a central opening known as a pupil 36. An aqueous zone of the eyeball is divided by the iris into an anterior chamber 38 and a posterior chamber 40. Prior to removal, the human lens 41 occupies the area anterior to the vitreous body 42 and posterior to the iris. In addition to the cornea 32, the eye is provided with another protective structure, the sclera 44 which joins the cornea in an area known as the trabecular meshwork 46. The aqueous humor is a fluid that comes from the ciliary processes 47 circulates from the posterior chamber 40 through the pupil 36 into the anterior chamber 38 to provide nourishment to the lens and cornea before passing out of the eye through the trabecular meshwork 46.

The haptics 14, 16 of lens 10 are positioned in either the ciliary sulcus 50, an area defined as the space between the root of the iris and the interior aspects of the ciliary body, or within the capsular bag 52. The haptics 14, 16 aid in proper placement of the lens 10 and further stablize the lens 10 in the eye.

Each haptic 14, 16 is a compressable, generally J shaped loop having a primary portion 18, 20 and a blocking segment 22, 24. The primary portions 18, 20 are conventional in the art. The blocking portions 22, 24 are sized and shaped to create a barrier which prevents the posterior capsule and ciliary process of the eye from inadvertantly moving forward to accidently occulude a standard trabeculectomy fistula.

As shown in FIG. 1, in a preferred embodiment, blocking segments 22, 24 are curved. When lens 10 is implanted in the eye, the blocking segments 22, 24 are posteriorly convex. This curved shaped, and the posterior convex orientation minimize inadvertant damage to the fragile posterior capsule and the posterior surface of the iris.

Each blocking segment 22, 24 has a chord length between about 1.5 to 4 mm, a thickness of about 0.5 mm and a wall thickness of about 0.280 mm. Each blocking segment 22, 24 forms an angle of about 170 degrees (170°) with its associated primary portions 18, 20. At its widest point each blocking portion 22, 24 has a width of at least about 1.50 mm.

To facilitate their blocking functions, both blocking segments 22, 24 have substantially continuous surfaces which define substantially circumferentially linear segments for contacting eye tissue over substantially their entire lengths. It is recognized that very small positioning or ventilation holes may be placed in the blocking segments without impairing their blocking function.

The blocking segments 22, 24, in effect, recreate the pre-surgical lens-iris diaphragm barrier to prevent the negative pressure created by the fistula from drawing the posterior capsule into the fistula site.

In use, when a cataract and filtration operations are combined, lens 10 is positioned such that at least one blocking segment is behind and in alignment with the trabeculectomy fistula. Thus, in place, the blocking segment can act as a barrier and prevent the posterior capsule ciliary process, and other tissue positioned posterior thereto from moving in front of said blocking segment to accidently occlude the trabeculectomy fistula. This in turn prevents interference with drainage of the aqueous humor from the fistula.

Lens 10 with blocking segments 22, 24 is useful not only during a combined cataract and filtration operation, it is also useful when placed in an eye prior to a filtration operation. Thus, if subsequent filtration surgery is necessary, the trabeculectomy site can be chosen directly over where one of the blocking segments is positioned. Not only will the operation have a greater chance of succeeding as a longterm plugging of the fistula site will be prevented by the blocking segments, but the surgery itself will be easier. When performing a trabeculectomy, after the limbal tissue is cut away, the first thing presenting to the wound is the iris. When one cuts into the eye all the mobile tissue tends to rush to the hole to plug it. A large iridectomy is made and flow of aqueous through this hole occurs. In an intracapsular aphakic eye after the iris is cut, vitreous enters to plug the hole. A vitrectomy of various depths is performed and aqueous percolates through the fistula site for a variable period of time until the hole is once again plugged by the omnipresent and viscous vitreous. In extracapsular phakia, the posterior capsule rushes in to plug the hole. If a vitrectomy were to be performed in this case, the posterior capsule would have to be repuntured and a vitrectomy perfomed recreating the same problems as occured in intracapsular aphakia with glaucoma. If a prior art lens were present in such a patient, this procedure would be extremely difficult and risky. The presence of an implant lens 10 with this blocking segments 22, 24 circumvents the foregoing problems.

What is claimed:

1. A posterior chamber intraocular lens usable as an implant in cataract patients, the lens comprising:
    an optic capable of performing the focusing function of a human lens;
    a first haptic having a substantially continuous surface and being connected to said optic;
    a second haptic having a substantially continuous surface and being connected to said optic; and
    a first blockiing segment connected to said first haptic, said first blocking segment having a chord length of at least 1.5 mm and having a width of at least 1.5 mm and defining a substantially circumferentially linear segment for contacting eye tissue over substantially its entire length, said first blocking segment being curved and when, in an eye, positioned such that it is posteriorly convex;
    said first blocking segment being sufficiently rigid to retain its shape;
    said first and second haptics being sufficiently flexible to permit insertion of the lens behind a pupil while being sufficiently rigid to avoid bending or pulling in response to a negative pressure;
    said first and second haptics both being vaulted in an anterior direction away from said optic.

2. The lens of claim 1 wherein both said first and said second haptics are generally J shaped.

3. The lens of claim 1 wherein the lens is a one piece construction made of PMMA.

4. The lens of claim 1 wherein both said first and said second blocking segments have a thickness of about 0.5 mm and a wall thickness of about 0.280 mm.

5. The lens of claim 1 further comprising a second blocking segment having a substantially continuous surface and being connected to said second haptic, said second blocking segment shaped and dimensioned substantially similarly to said first blocking segment, said second blocking segment, when in an eye, positioned such that it is posteriorly convex said second blocking segment being sufficiently rigid to retain its shape.

* * * * *